United States Patent [19]

Mok et al.

[11] Patent Number: 5,219,597
[45] Date of Patent: Jun. 15, 1993

[54] METHOD FOR PRODUCING HIGHLY CONCENTRATED, LACTIC-ACID FERMENTED PRODUCT UTILIZING UNGROUND GRAINY RICE AND IMPROVING QUALITIES THEREOF BY THE SECONDARY, ENZYMATIC TREATMENT AT FERMENTATION

[75] Inventors: Chul-Kyoon Mok; Young-Jung Nam; Young-Jin Kim, all of Seoul, Rep. of Korea

[73] Assignee: Korea Food Research Institute, Kyounggi-do, Rep. of Korea

[21] Appl. No.: 802,419

[22] Filed: Dec. 4, 1991

[30] Foreign Application Priority Data

Feb. 20, 1991 [KR] Rep. of Korea .................. 91-2747

[51] Int. Cl.$^5$ ............................................. A23L 1/22
[52] U.S. Cl. .................................. 426/28; 426/18
[58] Field of Search ............................ 426/18, 28

[56] References Cited

U.S. PATENT DOCUMENTS 3,615,697 10/1971 Hollenbeck ......................... 426/18
4,298,619 11/1981 Mutai et al. ......................... 426/43
4,876,096 10/1989 Mitchell et al. .................. 426/61 X Primary Examiner—Joseph Golian
Attorney, Agent, or Firm—Birch, Stewart, Kolasch & Birch

[57] ABSTRACT

Disclosed is a method for producing a highly concentrated, rice-derived lactic acid fermented product which tastes highly sweet and sour, and of which the flavor and texture are excellent. In this method, unground, grainy rice is gelatinized and then it is liquefied and saccharified by the primary treatment with α-amylase and glucoamylase. After sterilization, it is inoculated with lactic acid bacteria and undergoes a secondary treatment with α-amylase and glucoamylase. The glucose produced thereby continuously ferments to lactic acid. Finally, high concentrated lactic fermented product, tasting sweet and sour, and having excellent flavor and texture, is produced.

6 Claims, 3 Drawing Sheets

A: CONTROL
B: 0.02% α – AMYLASES TREATMENT
C: 0.02% α – AMYLASES & 0.02% GLUCOAMYLASES TREATMENT
D: 0.06% α – AMYLASES & 0.06% GLUCOAMYLASES TREATMENT

METHOD FOR PRODUCING HIGHLY CONCENTRATED, LACTIC-ACID FERMENTED PRODUCT UTILIZING UNGROUND GRAINY RICE AND IMPROVING QUALITIES THEREOF BY THE SECONDARY, ENZYMATIC TREATMENT AT FERMENTATION

FIELD OF THE INVENTION

The present invention relates to a method for producing a highly concentrated lactic-acid product fermented from rice, tasting sweet and sour, and having excellent flavor and texture.

In particular, the present invention relates to a method for producing the product comprising the steps of gelatinizing grainy rice which has not been ground, treating the gelatinized rice with α-amylase and glucoamylase thereby to producing glucose from rice-starch, which is a substrate for lactic acid fermentation, and producing lactic acid continuously by lactic acid fermentation.

SUMMARY OF THE INVENTION

The present invention is directed to a method for producing a highly concentrated, rice-derived lactic acid fermented product which tastes sweet and sour comprising the steps of immersing unground, grainy rice in water to gelatinize it, treating the gelatinized rice with an amylolytic enzyme containing α-amylase and glucoamylase to liquefy and saccharify it, heating the saccharified solution to inactivate the amylolytic enzyme and to sterilize the solution at the same time, inoculating the sterilized solution with a starter containing Streptococcus and Lactobacillus, fermenting the solution at high concentration, and homogenizing the fermented solution.

The present invention is also directed to a method for improving the qualities of a rice-derived, lactic acid fermented product which tastes highly sweet and sour, and of which the flavor and texture are excellent, comprising the steps of immersing unground, grainy rice in water to gelatinize, treating the gelatinized rice with amylolytic enzyme including α-amylase and glucoamylase to liquefy and saccharify it, heating the saccharified solution to inactivate the amylolytic enzyme and to sterilize the solution at the same time, inoculating the sterilized solution with a starter containing Streptococcus and Lactobacillus, fermenting the solution at high concentration, simultaneously with the secondary addition of amylolytic enzyme including α-amylase and glucoamylase in a bacteria-free state to produce glucose, which is a substrate for lactic acid fermentation, and homogenizing the fermented solution, whereby the glucose produced by the secondary enzymatic treatment is continuously fermented into lactic acid providing the final product with plenty of oligoosaccharides, monosaccharides, and lactic acid.

The Streptococcus of both processes discussed above may be Streptococcus thermophilus. The Lactobacillus of both processes discussed above may be Lactobacillus acidophilus, Lactobacillus bulgaricus, or Lactobacillus plantarum.

The mixing ration of Streptobacillus and Lactobacillus is 1 to 1.

Figure 1:
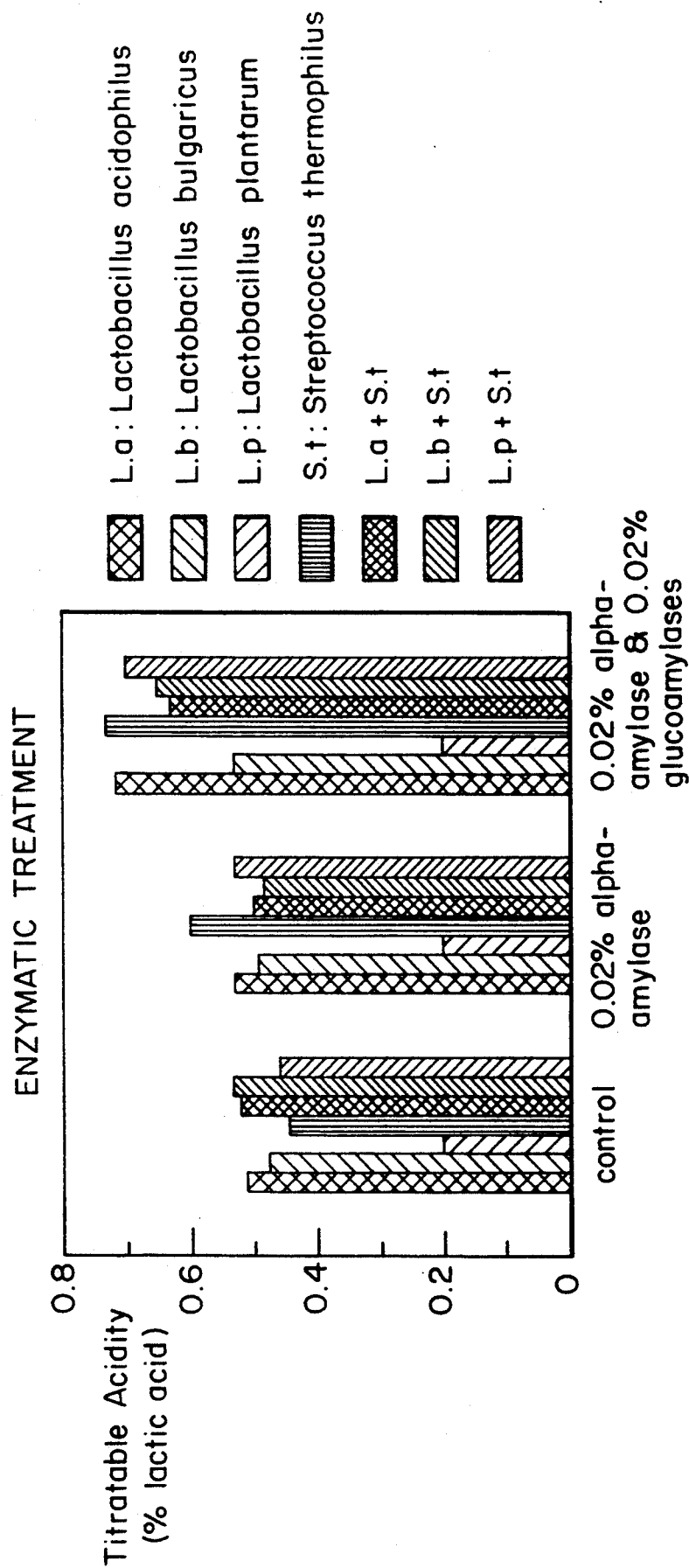
FIG. 1 is a graph showing the effect of acid-production in rice-derived, lactic acid fermented product by the secondary enzymatic treatment according to the present invention.

Hereunder, the present invention is described in detail. In the specification, all % is by weight unless specified otherwise.

DETAILED DESCRIPTION OF THE INVENTION (1) Gelatinization of rice

Rice used in the invention was "Sunchang, Junrabuk-Do" in Korea in 1989. When ground rice suspended in water is gelatinized, the viscosity of the suspension increases greatly and therefore, it is hard to stir the suspension. Accordingly, it is almost impossible to stir the suspension uniformly at a solution concentration of 10–15%. Furthermore, the heat transfer rate of the solution becomes decreased due to its high viscosity, thereby increasing energy consumption.

In the present invention unground, grainy rice is immersed in water at 40°–50° C. for 30 minutes (rice = 1:1.25 part by weight), followed by heating the same at 100° C. for 30 minutes to gelatinize the starch thereof.

(2) Primary liquefaction, saccharification and sterilization

Enzymes used in the invention were α-amylase (90 units/mg, manufactured by Sigma Chemical Co., St. Louis, MO., U.S.A.) and glucoamylase (8400 units/g, Sigma Chemical Co., St. Louis, MO., U.S.A.)

A 50–75% enzyme solution containing 0.1% of amylase and 0.1% of glucoamylase is added to the gelatined rice at 55° C. for 1–2 hours, to simultaneously liquefy and saccharify the same simultaneously. Optimum sweetness after saccharification is determined as about 15°–20° Brix. If too much saccharification is conducted, the too much, sweetness of the solution increases too much, inhibiting the growth of lactic acid bacteria due to its high osmotic pressure. The inventors have tried to provide sweetness of the solution suitable for the growth of lactic acid bacteria, employing the enzymes for liquefaction and saccharification which are inactivated by heating at 95° C. for 30 minutes, which also results in sterilization of the solution.

(3) Fermentation with secondary enzymatic treatment

Lactic acid bacteria used in the invention are three species of lactobacillus and one species of Streptococcus. The lactic acid bacteria which can be used in the invention are selected from one or more species from the group consisting Strephococcus thermophilus, Lactoba cillus, acidophilus and L. bulgaricus. L. plantarum bacteria can also be used only if they conduct a lactic acid fermentation from rice. Lactic acid bacteria used in the invention were Lactobacillus acidophilus ATCC 11506, L. bulgaricus KCTC 2179 and L. Plantarum ATCC 8014, and Streptococcus thermophilus KCTC 2185.

The lactic acid bacteria can be used alone or a mixture of one of those three Lactobacillus and Streptococcus thermophilus KCTC 2185,a mixing ratio being 1:1, can be used, also. The lactic acid bacteria are added thereto in an amount of 2%, which have been activated in a rice-saccharified solution.

A starter of lactic-acid bacteria is inoculated therewith and the saccharified solution is treated with sterilized, bacteria-free enzymatic solution in which α-amylase alone or α-amylase mixed with gluco-amylase is contained.

By the treatment with the enzymatic solution, rice-starch is hydrolyzed into glucose, which is a substrate for lactic-acid fermentation, so that glucose is continuously fermented into lactic acid to obtain a fermented product tasting highly sweet and sour. The fermentation is conducted at 37° C. and completed after 15-30 hours. After the (fer) mentation the fermented solution is homogenized by a homogenizer (Nissei AM-8, manufactured by Nihonseiki Kaisha Ltd, Japan) to obtain the final product.

After fermentation for 18 hours, acid-production has been increased greatly due to the secondary enzymatic treatment, compared with a control plot. Also, acid-production with Lactobacillus plantarum appears small but production with the mixed culture (with Streptococcus thermophilus) improves greatly. Generally, acid-production appears larger when fermented by a mixture of Lactobacillus and Streptococcus thermophilus however, acid-production appears small when fermented by Lactobacillus alone.

Figure 2:
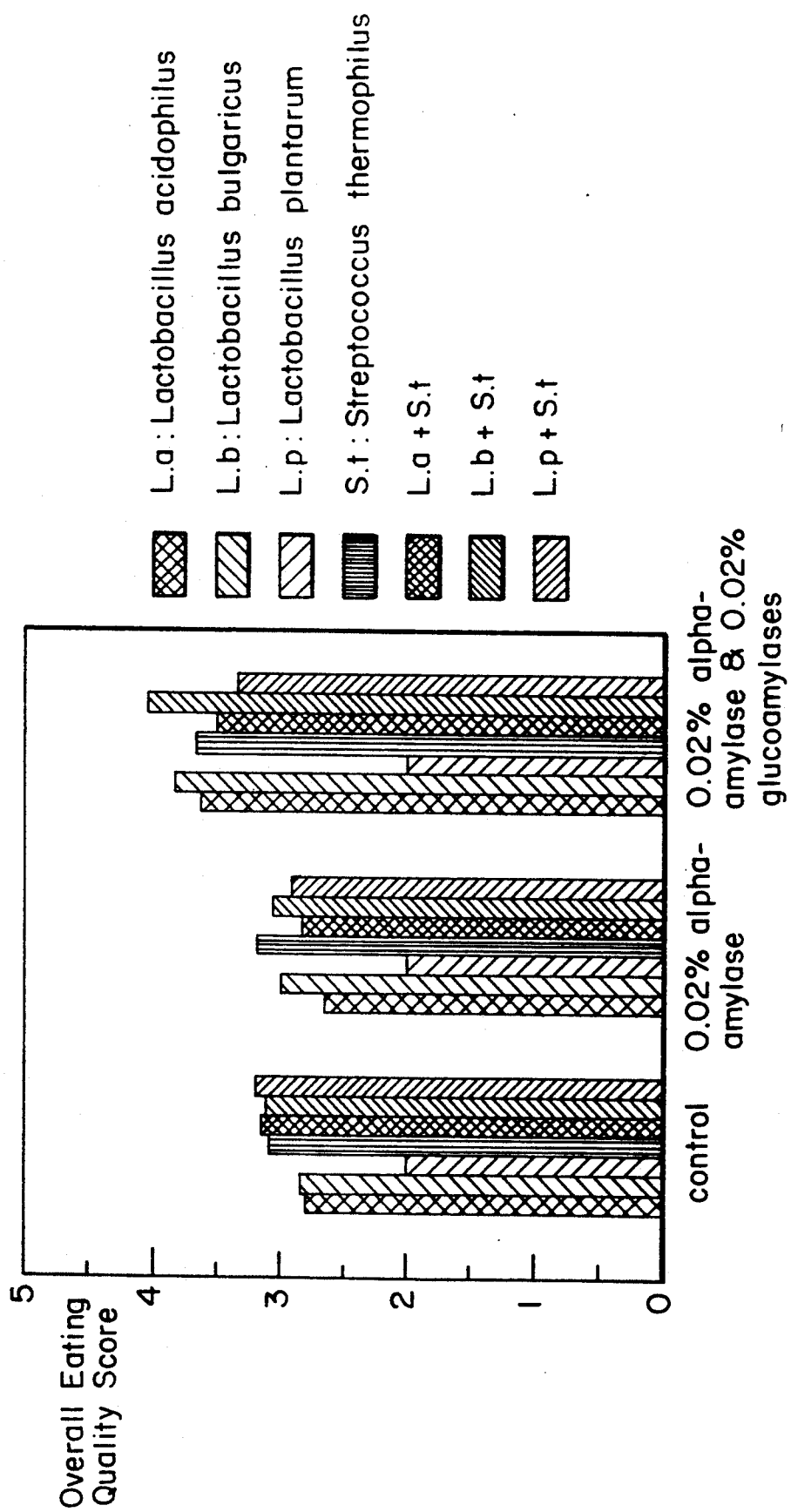
FIG. 2 is a graph showing the effect of overall preference in rice-derived, lactic-acid fermented product by the secondary enzymatic treatment according to the present invention.

The results of the organoleptic test for the product fermented for 18 hours are shown in FIG. 2. The organoleptic test (sensory evaluation) which was repeated three times, was conducted by six trained panel members and was evaluated by a 5-point method.

| | |
|---|---|
| Very good | 5 scores |
| Good | 4 scores |
| Fair | 3 scores |
| Bad | 2 scores |
| Very bad | 1 scords |

In consideration of the effects of the secondary enzymatic treatment, the treatment plot with 0.02% of α-amylase reveals no significant difference compared with the control plot; however the treatment with each 0.02% of α-amylase and glucomylase brings about significant improvement in the overall preference (overall eating quality score). Furthermore, examining the overall preference according to the species of lactic acid bacteria, we have found out that the best preference is obtained when the fermentation is conducted by the mixed Lactobacillus bulgaricus and Streptococcus thermophilus, the mixing ratio being 1:1, and each 0.02% of each of α-amylase and glucoamylase are used.

Figure 3:
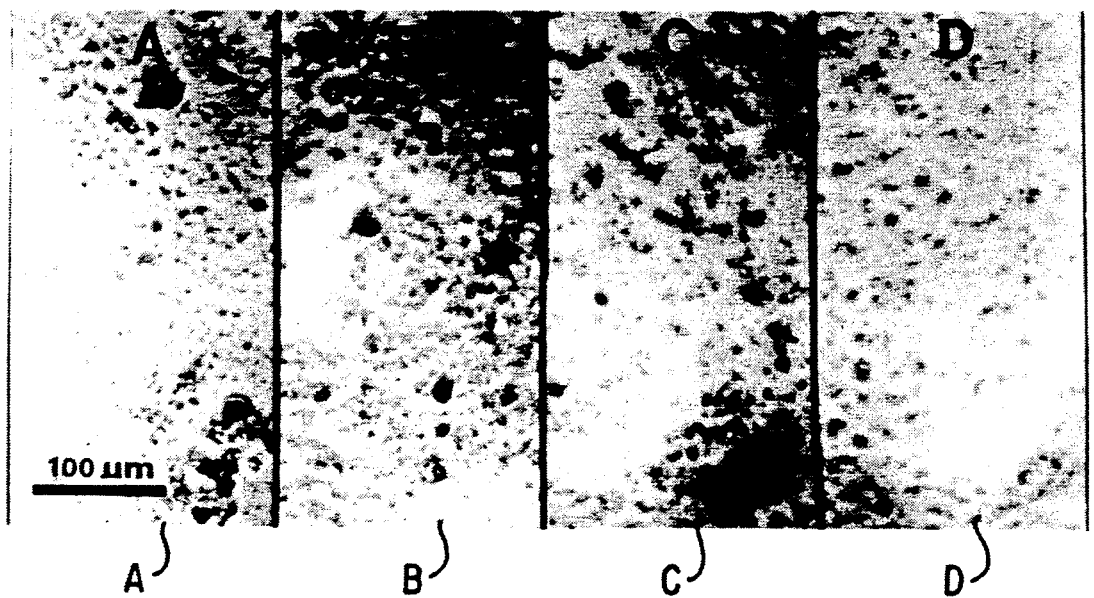
FIG. 3 is a photomicrograph showing micro-structure of rice-derived, lactic acid fermented product which has been treated secondarily with the enzyme according to the present invention.

The micro-structure of the product treated with the secondary enzymes, as shown in FIG. 3, brings about a conspicuous reduction in the size of insoluble solid particles, so that the texture in the mouth increases greatly. While not wishing to be bound by any theory, it is believed that insoluble solid portions are caused by the retrogradation of starch, and that the secondary enzymatic treatment prevents starch from retrogradation thereby reducing the size of the solid portion.

It is generally accepted that the critical particle size to be sensed extraneous in the mouth is about 20 μm. The insoluble solids which have been treated with the fermenting strain and the secondary enzymes according to the present invention were measured by a microscope equipped with a micrometer, and the results are shown in Table 1.

TABLE 1

The effects of the particle size in insoluble solid portions of rice-derived, lactic acid fermented product by the secondary enzymatic treatment at fermentation.

| | particle size (μm) | | |
|---|---|---|---|
| lactic acid bacteria | control | 0.02% α-amylase | 0.02% α amylase + 0.02% glucoamylase |
| L. acidophilus (L.a.) | 27.0 | 11.8 | 8.2 |
| L. bulgaricus (L.b.) | 17.4 | 14.5 | 8.9 |
| L. plantarum (L.p.) | 23.0 | 21.0 | 12.8 |
| S. thermophilus (S.t.) | 20.6 | 8.8 | 6.9 |
| L.a. + S.t. | 22.7 | 10.5 | 12.5 |
| L.b. + S.t. | 24.2 | 13.5 | 9.3 |
| L.p. + S.t. | 19.8 | 10.3 | 8.1 |

The control, which has not been treated with the secondary enzymes, reveals 17-27 μm in average particle size, whereas the product which has been treated with 0.02% of α-amylase caused reduction of particle size to reach 9-21 μm. The product which has been treated with 0.02% of each of α-amylase and glucoamylase brings about a remarkable reduction of particle size to reach 7-13 μm thereby great contributing toward the improvement in texture.

Lactobacillus bulgaricus and Streptococcus thermophilus selected as improved strains, were used to ferment rice for 18 hours, and the effects of the secondary enzymatic treatment on organoleptic elements are shown in Table 2 with respect to the fermented product thereby obtained.

TABLE 2

The effects to organoleptic elements of rice-derived, lactic acid fermented product with the secondary enzymatic treatment at fermentation

| Condition for secondary enzymatic treatment | Organoleptic elements | | | | |
|---|---|---|---|---|---|
| | flavor | taste | smoothness | consistency | overall preference |
| Control | 3.2A | 3.8BC | 3.7A | 3.3A | 2.8C |
| 0.02% α-amylase | 3.4A | 2.9C | 2.7B | 3.0A | 3.8BC |
| 0.02% α-amylase + 0.02% glucoamylase | 3.6A | 4.0AB | 3.7A | 2.8A | 3.8AB |
| 0.06% α-amylase + 0.06% glucoamylase | 3.5A | 4.3A | 4.0A | 2.7A | 4.3A |

*There is no significant difference at 5% level with respect to the scores marked by the same character in each organoleptic element.

The effects of the secondary enzymatic treatment with respect to preference of flavor, smoothness and consistency reveals no significant difference but remarkable improvements were observed in taste and overall preference.

Significant difference was not recognized between the case treated with 0.02% of each of α-amylase and glucoamylase and the other case treated with 0.06% of each of the same; therefore, the proper level in which α-amylase and glucoamylase are added thereto is determined as 0.02% each of both enzymes.

The properties of the product treated with each of 0.02% of α-amylase and glucoamylase at fermentation using *Lactobacillus bulgaricus* and *Streptococcus thermophilus* according to said procedures are shown in Table 3.

TABLE 3

Properties of rice-derived lactic acid fermented product

| Item | |
|---|---|
| pH | 2.95 |
| acidity (%) | 0.53 |
| moisture content (%) | 76.10 |
| solid (%) | 23.90 |
| protein (%) | 2.00 |
| sweetness (° Brix) | 24.00 |
| number of viable bacteria per ml | $1.54 \times 10^8$ |
| apparent viscosity (mPa s) | 35 (shear rate $100s^{-1}$) |

EXAMPLE

Rice immersed in water or crushed rice obtained during milling (rice: water = 4:5 parts by weight) was heated for 30 minutes to gelatinize, followed by the addition of 75% of amylase-solution containing 0.1% of α-amylase and 0.1% of glucoamylase to the gelatinized rice, thereby to saccharifying the same for 1-2 hours. Thereafter, a starter containing 1% of each of *Lactobacillus bulgaricus* and *Streptococcus thermophilus* which have been activated in a rice-saccharified solution was added and 0.02% of each enzyme (α-amylase and glucoamylase) sterilized by passing through a bacteria-free filter was added thereto at 37° C. to ferment for 15-30 hours. After homogenization, the highly concentrated, rice-derived lactic acid fermented product without any additives such as sugar and acid was obtained, which tasted sweet and sour, and of which the flavor and texture were excellent.

We claim:

1. A method for producing a highly concentrated, rice derived lactic acid fermented product having a sweet and sour taste, which comprises:

gelatinizing unground, grainy rice by immersing said rice in water and heating to form a gelatinized rice product;

liquefying and saccharifying said gelatinized rice product by treating said gelatinized rice product with a sufficient amount of an amylolytic enzyme containing α-amylase and glycoamylase to form a saccharified solution;

inactivating said amylolytic enzyme and sterilizing said saccharified solution by heating to form a sterilized solution;

inoculating said sterilized solution with a starter containing a microorganism selected from each of the genuses Streptococcus and Lactobacillus, to form an inoculated solution;

fermenting said inoculated solution to form a fermented solution; and homogenizing said fermented solution, to obtain said highly concentrated rice-derived lactic acid fermented product.

2. The method according to claim 1, wherein said microorganism selected from the genus Streptococcus is *Streptococcus thermophilus* and said microorganism selected from the genus Lactobacillus is selected from the group consisting of *Lactobacillus acidophilus*, *Lactobacillus bulgaricus*, and *Lactobacillus plantarum*.

3. The method according to claim 1, wherein said starter contains said microorganism selected from the genus Streptococcus and said microorganism selected from the genus Lactobacillus in a mixing ratio of 1:1.

4. A method for improving the flavor and texture qualities of a rice-derived lactic acid fermented product having sweet and sour taste, which comprises:

gelatinizing unground, grainy rice by immersing said rice in water and heating to form a gelatinized rice product;

liquefying and saccharifying said gelatinized rice product by treating said gelatinized rice product with a sufficient amount of an amylolytic enzyme containing α-amylase and glycoamylase to form a saccharified solution;

inactivating said amylolytic enzyme and sterilizing said saccharified solution by heating to form a sterilized solution;

inoculating said sterilized solution with a starter containing a microorganism selected from each of the genuses Streptococcus and Lactobacillus, to form an inoculated solution;

fermenting said inoculated solution while simultaneously adding an amylolytic enzyme containing α-amylase and glycoamylase in a bacteria-free state in sufficient amounts to produce glucose, whereby said glucose produced is continuously fermented into lactic acid, to form a fermented solution; and homogenizing said fermented solution, to obtain said highly concentrated, rice-derived lactic acid fermented product.

5. The method according to claim 4, wherein said microorganism selected from the genus Streptococcus is *Streptococcus thermophilus* and said microorganism selected from the genus Lactobacillus is selected from the group consisting of *Lactobacillus acidophilus*, *Lactobacillus bulgaricus*, and *Lactobacillus plantarum*.

6. The method according to claim 4, wherein said starter contains said microorganism selected from the genus Streptococcus and said microorganism selected from the genus Lactobacillus in a mixing ration of 1:1.

* * * * *